(12) United States Patent
Ramanjaneyulu et al.

(10) Patent No.: US 8,048,904 B2
(45) Date of Patent: Nov. 1, 2011

(54) PROCESS FOR THE PREPARATION OF OLMESARTAN MEDOXOMIL

(75) Inventors: Gorantla Seeta Ramanjaneyulu, Hyderabad (IN); Bandari Mohan, Hyderabad (IN); Purna Chandra Ray, Hyderabad (IN); Madhuresh Kumar Sethi, Hyderabad (IN); Vijendra Singh Rawat, Hyderabad (IN); Yerramalla Raja Krishna, Hyderabad (IN); Vemula Lakshminarayana, Hyderabad (IN); Mamidi Srinivas, Hyderabad (IN)

(73) Assignee: Matrix Laboratories Ltd., Secunderabad (IN)

( * ) Notice: Subject to any disclaimer, the term of this patent is extended or adjusted under 35 U.S.C. 154(b) by 367 days.

(21) Appl. No.: 12/305,512

(22) PCT Filed: Jun. 15, 2007

(86) PCT No.: PCT/IN2007/000238
§ 371 (c)(1), (2), (4) Date: Dec. 18, 2008

(87) PCT Pub. No.: WO2007/148344
PCT Pub. Date: Dec. 27, 2007

(65) Prior Publication Data
US 2009/0281327 A1  Nov. 12, 2009

(30) Foreign Application Priority Data

Jun. 19, 2006 (IN) .......................... 1046/CHE/2006
Dec. 27, 2006 (IN) .......................... 2427/CHE/2006

(51) Int. Cl.
*A61K 31/41* (2006.01)
*C07D 405/14* (2006.01)
(52) U.S. Cl. ................... 514/382; 548/252; 548/254
(58) Field of Classification Search ................... None
See application file for complete search history.

(56) References Cited

FOREIGN PATENT DOCUMENTS
WO  WO 2007017135 A2 *  2/2007
* cited by examiner

*Primary Examiner* — Yong Chu
*Assistant Examiner* — Michael Barker
(74) *Attorney, Agent, or Firm* — Ladas & Parry LLP

(57) ABSTRACT

The present invention provides a process for the preparation of Olmesartan medoxomil by condensing the ethyl 4-(1-hydroxy-1-methylethyl)-2-propylimidazole-5-carboxylate with 4-[2-(trityl tetrazol-5-yl)phenyl]benzyl bromide to obtain ethyl 4-(1-hydroxy-1-methyl ethyl)-2-propyl-1-{4-[2-(trityl tetrazol-5-yl)phenyl]phenyl}methylimidazole-5-carboxylate and then hydrolyzing ethyl 4-(1-hydroxy-1-methyl ethyl)-2-propyl-1-{4-[2-(trityl tetrazol-5-yl)phenyl]phenyl}methyl imidazole-5-carboxylate to obtain trityl Olmesartan dihydrate followed by reacting trityl Olmesartan dihydrate with 4-chloromethyl-5-methyl-2-oxo-1,3-dioxolene to obtain trityl Olmesartan medoxomil and then deprotecting trityl Olmesartan medoxomil to obtain Olmesartan medoxomil.

19 Claims, 5 Drawing Sheets

PROCESS FOR THE PREPARATION OF OLMESARTAN MEDOXOMIL

This application claims the benefit of Indian Provisional Application No. 1046/CHE/2006 filed on Jun. 19, 2006 and Indian Provisional Application No. 2427/CHE/2006 filed on Dec. 27, 2006, both of which are hereby incorporated by reference

FIELD OF INVENTION

The present invention relates to process for the preparation of Olmesartan medoxomil

BACKGROUND OF THE INVENTION

Olmesartan medoxomil, 4-(1-hydroxy-1-methylethyl)-2-propyl-1-[[2'-(1H-tetrazol-5-yl)[1,1'-biphenyl]-4-yl]methyl]-1H-imidazole-5-carboxylic acid has the formula as given below:

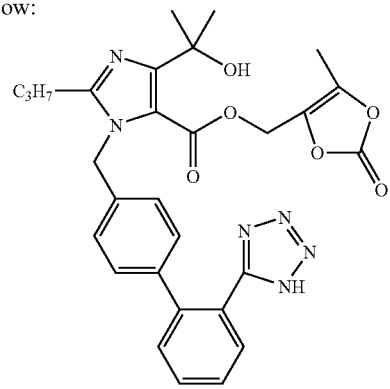

Olmesartan medoxomil is found to be an excellent Angiotensin II receptor antagonist activity and is therefore useful as antihypertensive drug and for the therapy and prophylaxis of heart diseases.

U.S. Pat. No. 5,616,599 discloses a process for the preparation of Olmesartan medoxomil comprising
  Condensing the ethyl 4-(1-hydroxy-1-methylethyl)-2-propylimidazole-5-carboxylate with 4-[2-(trityl tetrazol-5-yl)phenyl]benzyl bromide in presence of NaH/DMF to obtain ethyl 4-(1-hydroxy-1-methyl ethyl)-2-propyl-1-{4-[2-(trityl tetrazol-5-yl)phenyl]phenyl}methyl imidazole-5-carboxylate
  Reacting the above; obtained compound with lithium hydroxide in dioxane to obtain corresponding lithium carboxylate, which is then reacted with 4-chloromethyl-5-methyl-2-oxo-1,3-dioxolene in presence of $K_2CO_3$/DMA and the obtained residue is subsequently crystallized from IPE to obtain trityl Olmesartan medoxomil, which is then deprotected in presence of acetic acid/water followed by crystallization in ethyl acetate to obtain Olmesartan medoxomil U.S. Pat. No. 5,744,612 discloses a process for producing Olmesartan and Olmesartan alkyl ester comprising the step of reacting ethyl ester of 1-(2'-cyanobiphenyl-4-yl)methyl-4-(1-hydroxy-1-methylethyl)-2-propylimidazole-5-carboxylic acid with an inorganic azide such as sodium azide in an aromatic hydrocarbon solvent such as toluene or xylene in the presence of an amine salt such as triethylamine hydrochloride to obtain Olmesartan ethyl ester followed by hydrolysis to Obtain Olmesartan The US'612 also discloses a process for preparing a 5-substituted tetrazole comprising the step of reacting a nitrile with an inorganic azide in aromatic hydrocarbon such as toluene or xylene in the presence of an amine salt such as triethylamine hydrochloride.

US 2005/0119488 claims the compounds containing cumyl tetrazolyl group or an isomer or tautomer thereof and claims a process for the deprotection of a compound containing cumyl tetrazolyl group by deprotecting the 4-(1-hydroxy-1-methylethyl)-2-propyl-1-{[4-2-(cumyltetrazol-5-yl)phenyl]phenyl}methylimidazole-5-carboxylic acid (cumyl Olmesartan) in presence of anhydrous HCl or HBr in an organic protic or aprotic solvents preferably MDC or EtOAc or toluene to produce 4-(1-hydroxy-1-methylethyl)-2-propyl-1-{[4'-tetrazol-5-yl)phenyl]phenyl}methyl imidazole-5-carboxylic acid (Olmesartan).

US 2006/0069141 discloses a process for the preparation of Olmesartan medoxomil in which trityl Olmesartan medoxomil is contacted with an acid in a mixture of water miscible organic solvent and water. Preferred water-miscible organic solvents include acetone, acetonitrile and t-butanol and most preferred solvent is acetone and water in about 1:3 to about 3:1 by volume. By the above process it is given that the impurity-Olmesartan acid is reduced to less than about 1% and the Olmesartan medoxomil is obtained directly without the evaporation step as given in the U.S. Pat. No. 5,616,599.

US 2006/00069141 discloses a process for preparing Olmesartan Medoxomil comprises
  Contacting trityl Olmesartan medoxomil with an acid in a water miscible organic solvent, with or without water, to obtain a solution of Olmesartan medoxomil and a precipitate of triphenyl carbinol,
  Separating the precipitate of triphenyl carbinol from the solution of Olmesartan medoxomil and contacting the solution of Olmesartan medoxomil with a base to obtain a precipitate of Olmesartan medoxomil.

US 2006/00069141 also describes the drawbacks of the prior art methods wherein Olmesartan medoxomil is isolated from acidic conditions contains around 2.2% Olmesartan acid impurity by HPLC.

US 2006/0074117 discloses a process for purifying Olmesartan Medoxomil comprising:
  contacting trityl Olmesartan medoxomil with an acid in a water-miscible organic solvent to obtain a solution of Olmesartan medoxomil and a precipitate of triphenyl carbinol,
  separating the precipitate of triphenyl carbinol from the solution of Olmesartan medoxomil and contacting the solution of Olmesartan medoxomil with a base to obtain a precipitate of Olmesartan medoxomil.
  recovering the precipitate of Olmesartan Medoxomil
  dissolving the precipitate of Olmesartan Medoxomil in a $C_{3-6}$ ketone and adding water to recover the purified Olmesartan Medoxomil.

OBJECTIVE OF THE INVENTION

The main object of the present invention is to provide a process for the preparation of Olmesartan medoxomil with high purity.

In another objective of the present invention is to perform the alkylation reaction in the presence of a catalyst.

In another objective of the present invention is to prepare novel trityl Olmesartan dihydrate In another objective of the present invention is to prepare a novel process for deprotection of trityl Olmesartan medoxomil

SUMMARY OF THE INVENTION

In an aspect of the present invention is to provide a process for the preparation of Olmesartan medoxomil which comprises
  i) alkylating the ethyl 4-(1-hydroxy-1-methylethyl)-2-propylimidazole-5-carboxylate with 4-[2-(trityl tetrazol-5- yl)phenyl]benzyl bromide in presence of catalyst and base in the organic solvent to obtain ethyl 4-(1-hydroxy-1-methylethyl)-2-propyl-1-{4-[2-(trityl tetrazol-5-yl) phenyl]phenyl}methylimidazole-5-carboxylate, ii) hydrolyzing ethyl 4-(1-hydroxy-1-methylethyl)-2-propyl-1-{4-[2-(trityl tetrazol-5-yl)phenyl]phenyl}methyl imidazole-5-carboxylate to obtain trityl Olmesartan dihydrate, iii) esterifying trityl Olmesartan dihydrate with 4-chloromethyl-5-methyl-2-oxo-1,3-dioxolene in the organic solvent in presence of base and catalyst to obtain trityl Olmesartan medoxomil, iv) deprotecting the trityl Olmesartan medoxomil to obtain Olmesartan medoxomil, The present invention describes another embodiment detailing an improved process for the preparation of Olmesartan medoxomil which comprises:

i) contacting trityl Olmesartan medoxomil with an acid in water and water-immiscible organic solvent
ii) separating aqueous and organic layers
iii) adjusting the pH of the aqueous layer with base
iv) extracting the resulting solution of step (iii) with water-miscible organic solvents and
v) isolating Olmesartan medoxomil

DETAILED DESCRIPTION OF THE INVENTION

Figure 1:
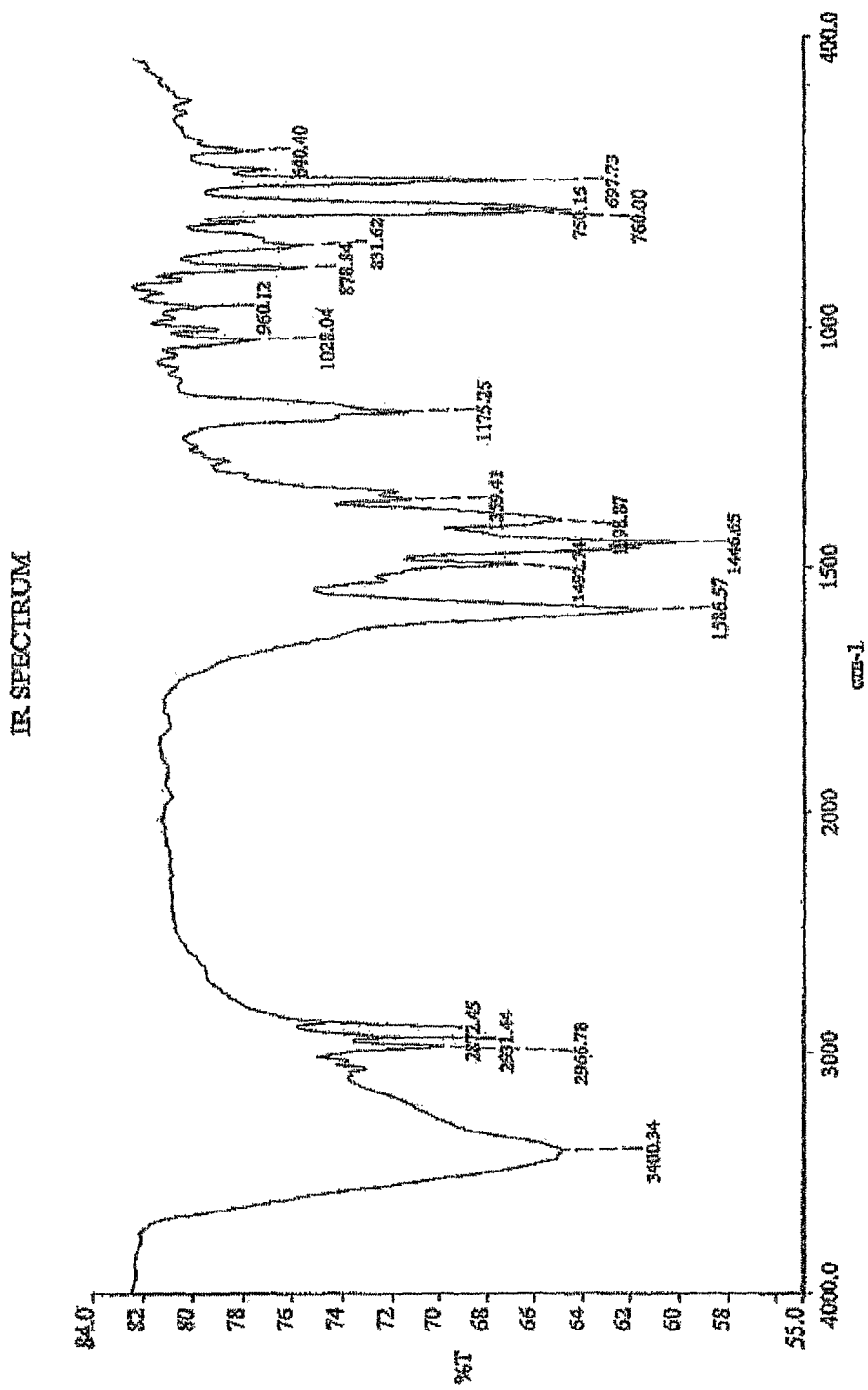
FIG. 1 represents IR spectrum of Novel trityl Olmesartan dihydrate
Figure 2:
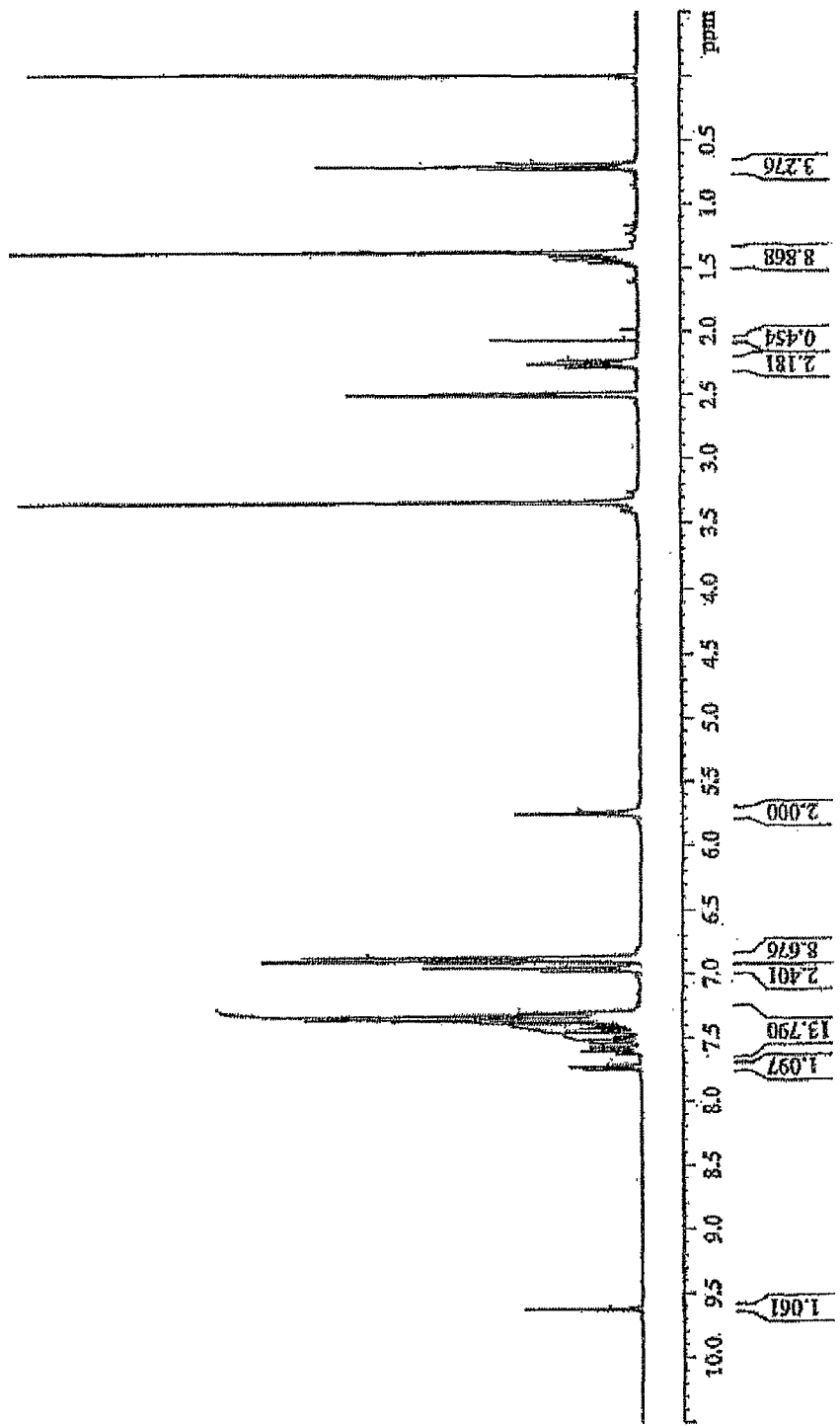
FIG. 2 represents NMR spectrum of Novel trityl Olmesartan dihydrate
Figure 3:
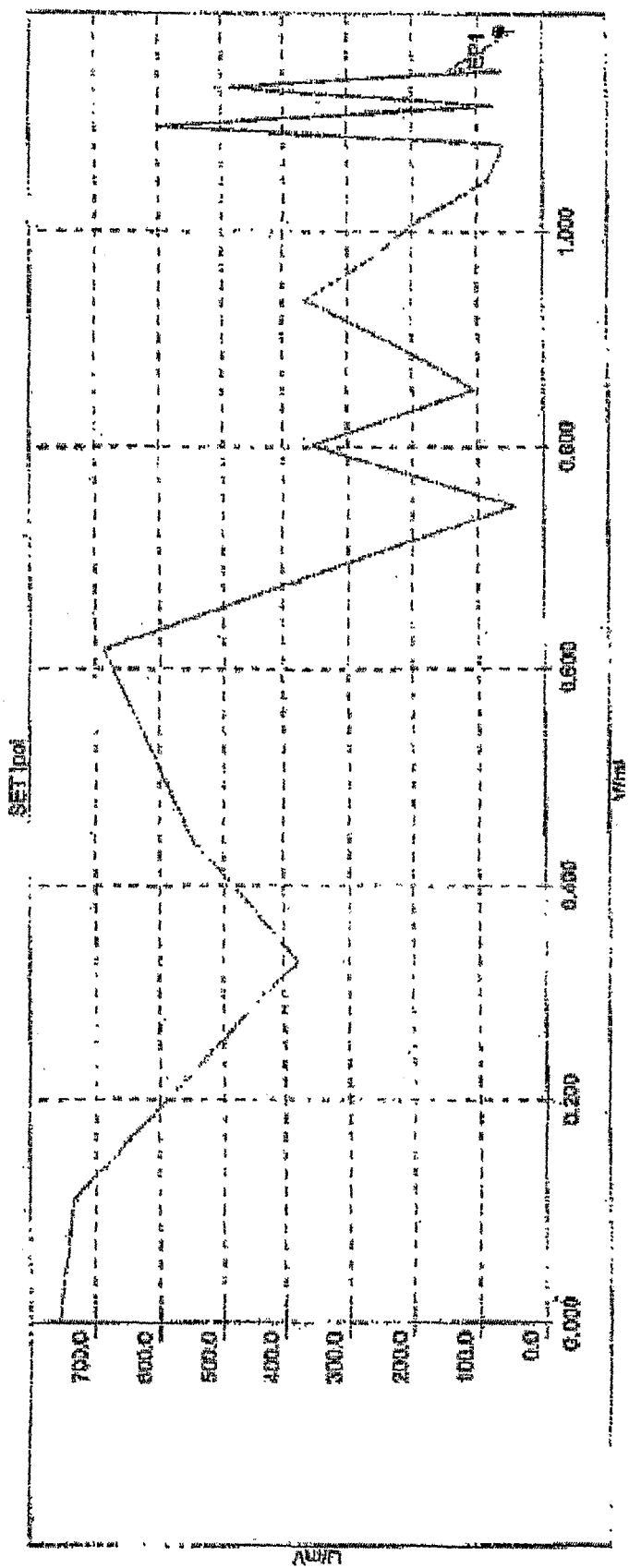
FIG. 3 represents Karl-Fisher data of Novel trityl Olmesartan dihydrate
Figure 4:
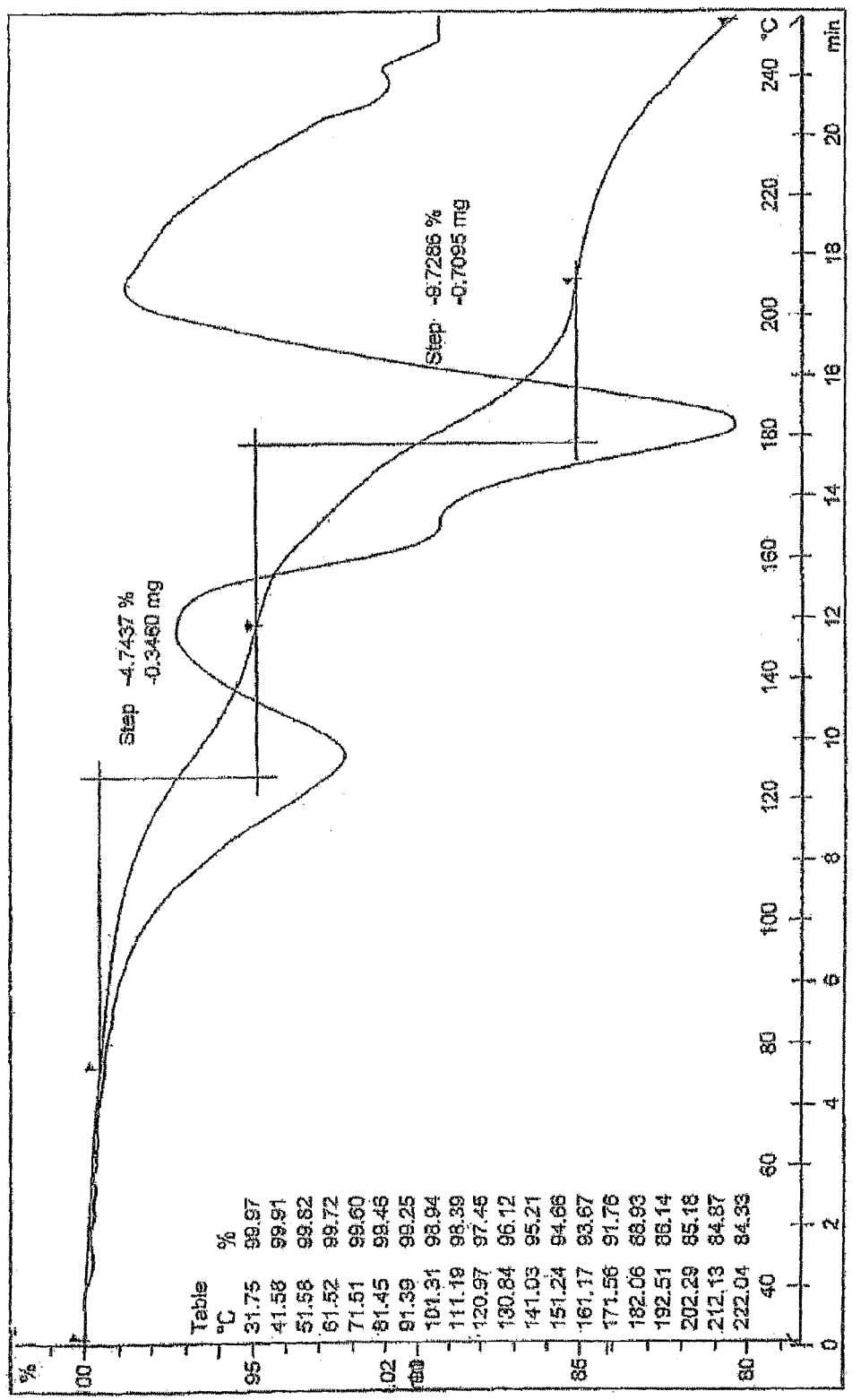
FIG. 4 represents TGA diagram of Novel trityl Olmesartan dihydrate
Figure 5:
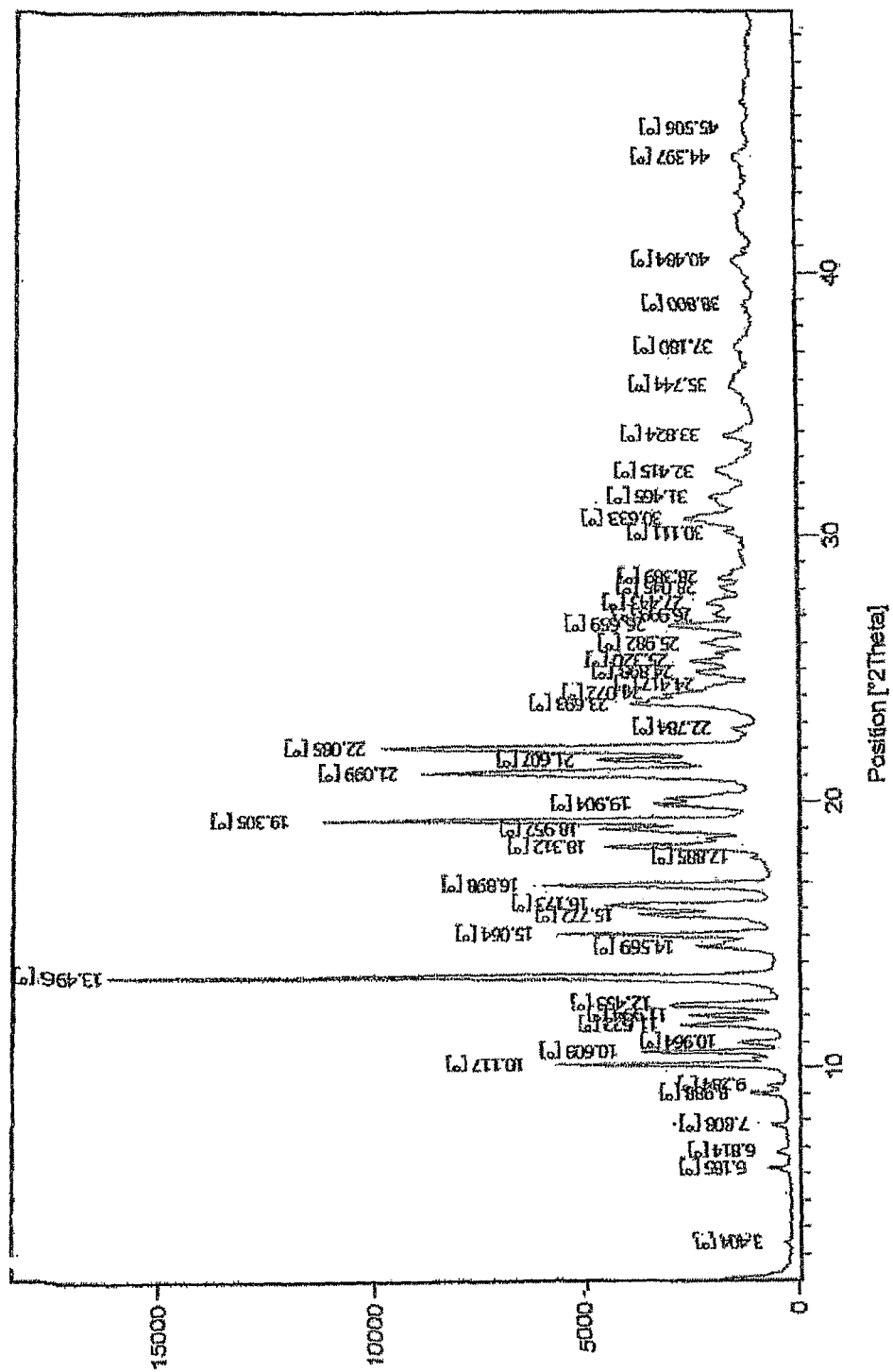
FIG. 5 represents XRD diagram of Novel trityl Olmesartan dihydrate

Thus in accordance with the present invention preparation of Olmesartan medoxomil comprises the following steps:

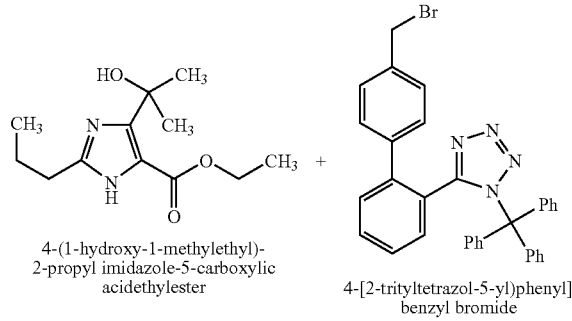

4-(1-hydroxy-1-methylethyl)-2-propyl imidazole-5-carboxylic acidethylester

4-[2-trityltetrazol-5-yl)phenyl] benzyl bromide

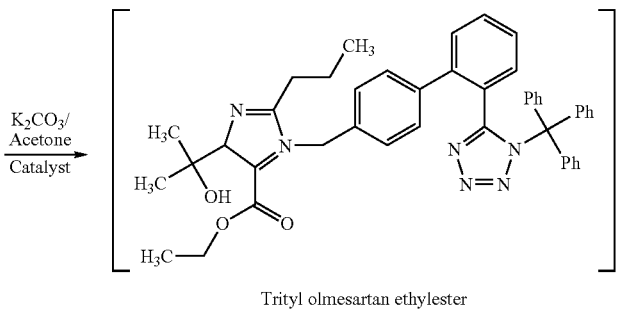

Trityl olmesartan ethylester

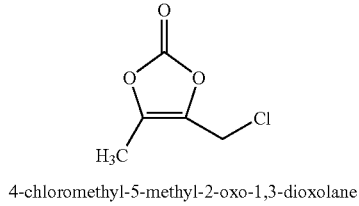

4-chloromethyl-5-methyl-2-oxo-1,3-dioxolane

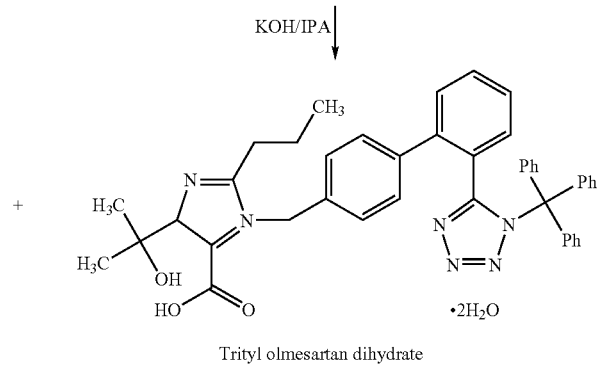

Trityl olmesartan dihydrate

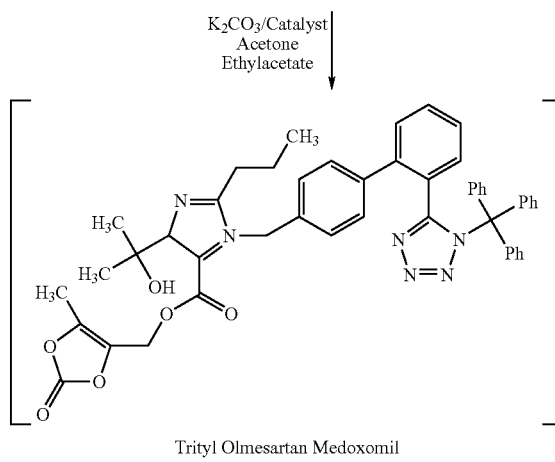

Trityl Olmesartan Medoxomil

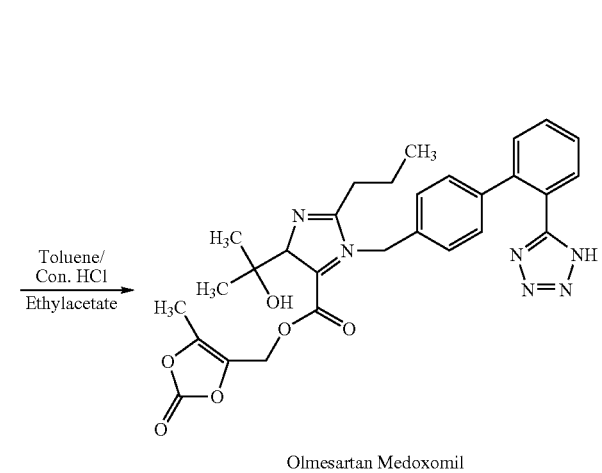

Olmesartan Medoxomil

In a specific embodiment, the present invention provides a process for the preparation of Olmesartan medoxomil, which involves condensing the ethyl 4-(1-hydroxy-1-methylethyl)-2-propylimidazole-5-carboxylate with 4-[2-(trityltetrazol-5-yl)phenyl]benzyl bromide in presence of a phase transfer catalyst using base in an organic solvent to obtain ethyl 4-(t-hydroxy-1-methylethyl)-2-propyl-1-{4-[2-(trityltetrazol-5-yl)phenyl]phenyl}methyl imidazole-5-carboxylate The catalysts employed in the above condensation reaction can be selected from phase transfer catalysts like tetrabutyl ammonium bromide, tetrapropyl ammonium bromide, tri butyl benzyl ammonium bromide, tetraoctyl ammonium bromide, tetrabutyl ammonium iodide, tetra butyl ammonium hydrogen sulphate, benzyl trimethyl ammonium chloride, benzyl triethyl ammonium chloride, tetrabutyl ammonium acetate, tetrabutyl ammonium iodide, ethyl triphenyl phosphonium bromide more preferably tetrabutyl ammonium bromide or alkyl iodides like sodium iodide, potassium iodide and lithium iodide.

The alkylation reaction is carried out in the presence of base selected from alkali metal carbonates such as sodium carbonate, potassium carbonate, alkali metal hydrides such as sodium hydride, potassium hydride or lithium hydride, alkali metal alkoxides such as sodium methoxide, sodium ethoxide, potassium t-butoxide or lithium methoxide, more preferably potassium carbonate.

The alkylation reaction is carried out in inert organic solvent selected from aromatic hydrocarbons such as benzene, toluene or xylene, ethers such as tetrahydrofuran or dioxane, alcohols such as methanol, ethanol, or t-butanol, amides such as N,N-dimethylacetamide, N,N-dimethylformamide or N-methyl-2-pyrrrolidinone, ketones such as acetone or methyl ethyl ketone, nitriles such as acetonitrile, sulfoxides such as dimethyl sulfoxide, more preferably acetone.

It has been unexpectedly found that in the preparation of Olmesartan medoxomil the allylation step goes to completion very quickly and also gives higher yields with low level of impurities. This has been accomplished by employing phase transfer catalyst. The compound obtained in this step is purified by recrystallization from toluene.

The ethyl 4-(1-hydroxy-1-methyl ethyl)-2-propyl-1-{4-[2-(trityl tetrazol-5-yl)phenyl]phenyl}methyl imidazole-5-carboxylate is hydrolyzed with bases that are selected from potassium hydroxide, sodium hydroxide etc in IPA yields trityl Olmesartan in its dihydrate form. The obtained trityl Olmesartan dihydrate is found to be novel.

The trityl Olmesartan is normally isolated as a lithium salt in prior-art. However, in the present process of the invention, the inventors have surprisingly found that trityl Olmesartan is isolated as dihydrate. The trityl Olmesartan dihydrate is characterized by IR, NMR, TGA and XRD and karl-Fisher. The trityl Olmesartan dihydrate obtained has a moisture content of 4-6.0% w/w and melting point in the range of 146-150° C. Also the trityl Olmesartan dihydrate obtained in the present process of the invention has potassium content in the range of about 0.1% w/w.

The inventors have further found that the trityl Olmesartan dihydrate form obtained has very good solubility which will facilitate easy dissolution for esterification step.

Esterification of trityl Olmesartan dihydrate with 4-chloromethyl-5-methyl-2-oxo-1,3-dioxolene in presence of catalytic amount of alkali idodide in using base in an organic solvent to give trityl Olmesartan medoxomil. This 4-chloromethyl-5-methyl-2-oxo-1,3-dioxolene is activated by addition of alkali iodide selected from potassium iodide, sodium iodide and lithium iodide, more preferably potassium iodide.

The esterification reaction is conducted in an organic solvent selected from N,N-dimethylformamide or NAN-dimethylacetamide, halogenated aliphatic hydrocarbons such as methylene chloride, ketones such as acetone or methyl, ethers such as tetrahydrofuran, dioxane more preferably acetone, The esterification is preferably carried out in the presence of bases selected from organic amine base such as triethylamine, pyridine, N-methyl morpholine, an alkali metal carbonate such as sodium carbonate or potassium carbonate, alkali metal hydrogen carbonates such as sodium hydrogen carbonate or potassium hydrogen carbonate, more preferably potassium carbonate.

Another advantage realized in the present process of the invention is that all the above three steps can be synchronously performed in one pot without isolation of the intermediates.

The deprotection of Olmesartan medoxomil involves reaction of trityl Olmesartan medoxomil with an acid in water and water-immiscible organic solvent to obtain Olmesartan medoxomil in aqueous solution. The aqueous solution is treated with a base and extracted with ethylacetate or methylene chloride to obtain Olmesartan medoxomil. Any suitable water-immiscible solvent may be used in the process of the invention. Preferably the immiscible solvent includes, but is not limited to, at least one of hydrocarbons such as benzene, cyclohexane, toluene, xylene, aliphatic solvents which includes halocarbons such as methylene chloride, chloroform, ketones such as methyl isobutyl ketone, and carboxylic esters such as ethyl acetate. Most preferred solvent is toluene.

The acid used is an acid with, a pH of about 0 to 4. Suitable acids include, but are not limited to, organic acids such as formic acid, acetic acid, benzoic acid, and oxalic acid, sulfuric acid, sulfurous acid, p-toluene sulfonic acid, nitric acid, nitrous acid, phosphoric acid, and carbonic acid, and binary acids such as hydrofluoric acid, hydrochloric acid, hydrobromic acid, hydrocyanic acid, and hydrosulfuric acid. Most preferably hydrochloric acid is used. Preferably the amount of acid is about 2 to about 8 equivalents.

Reaction temperature at which deprotection of trityl Olmesartan medoxomil takes place is preferable at about 0° C. to 60° C. more preferably at 10° C. to 30° C. In another preferred embodiment the combination of trityl Olmesartan medoxomil, water-immiscible organic solvent and acid is maintained for about 1 to 6 hours and more preferably 2 to 4 hours. Triphenyl carbinol formed dissolves in solvent toluene and the deprotected Olmesartan medoxomil is in aqueous solution. Both the layers are separated. Aqueous layer is washed with toluene and the pH of the aqueous layer is adjusted to about 5 to 6 using a base. Suitable bases include but are not limited to, alkali and alkaline earth metal hydroxides, carbonates, and hydrogen carbonate salts. Specific exemplary bases include, but are not limited to, sodium hydroxide, potassium hydroxide, calcium hydroxide, magnesium hydroxide, sodium carbonate, potassium carbonate, sodium bicarbonate, potassium bicarbonate, and calcium carbonate. Potassium carbonate and sodium bicarbonate are preferred. After contacting the solution with the base, the solution is extracted with ethyl acetate twice. Combined ethyl acetate layers are washed with 5% sodium chloride solution. Olmesartan medoxomil is obtained by distillation of the solvent.

The Olmesartan medoxomil obtained by the above process is purified by prior-art methods reported in literature.

EXAMPLES

The present invention will now be further explained in the following examples. However, the present invention should not be construed as limited thereby. One of ordinary skill in the art will understand how to vary the exemplified preparations to obtain the desired results.

Example 1

Preparation of 4-(1-Hydroxy-1-methylethyl)-2-propyl-1-{4-[2-(trityltetrazol-5-yl)phenyl]phenyl}methylimidazole-5-carboxylic Acid Dihydrate 4-(1-Hydroxy-1-methylethyl)-2-propyl-1H-imidazole-5-carboxylic acid ethyl ester (100 g), N-(triphenylmethyl)-5-(4'-bromomethyl biphenyl-2-yl) tetrazole (250 g), potassium carbonate (170 g) & tetra butyl ammonium bromide (15 g) in acetone (2.5 L) were refluxed for 10-16 hours. Progress of reaction was monitor by HPLC. Reaction mass was cooled & filtered to remove the salts. Inorganic salts were washed with acetone (300 ml). Acetone from combine the filtrate & washings was distilled. The residue obtained was refluxed with acetonitrile (500 ml). The reaction mass was cooled, filtered & solid after filtration was dissolved in Isopropyl alcohol (1500 ml). Separately prepared solution of potassium hydroxide (180 g) in IPA (2000 ml) was added slowly to above solution at room temperature. Reaction mass was stir for 2-4 hrs at 30-40° C. Isopropyl alcohol was distilled under reduced pressure. Water (1 000 ml), sodium chloride (100 g) & ethyl acetate (2000 ml) was added to the residue. Separate the two layers & aqueous layer was extracted with ethyl acetate (3×1000 ml). Combined ethyl acetate layer was washed with sodium bicarbonate solution (2×2000 ml) & dried ($Na_2SO_4$). Distilled off ethyl acetate under reduced pressure completely. Add acetonitrile (2000 ml) was added to the residue. The reaction mass was cooled, filtered, washed with acetonitrile (500 ml) & dried to get 4-(1-hydroxy-1-methylethyl)-2-propyl-1-{4-[2-(trityltetrazol-5-yl)phenyl]phenyl}methylimidazole-5-carboxylic acid dihydrate (250 g).

Purity by HPLC=97.0%

Example-2

Preparation of Olmesartan Medoxomil 4-(1-hydroxy-1-Methylethyl)-2-propyl-1-{4-[2-(trityltetrazol-5-yl)phenyl]phenyl}methyl imidazole-5-carboxylic acid dihydrate (250 g) in acetone (4000 ml) was added to suspension of potassium carbonate (50 g), potassium iodide (15 g) & 4-chloromethyl-5-methyl-1,3-dioxol-2-one (75 g) in acetone (1500 ml) at reflux temperature. Reaction mass was refluxed for 2-6 hrs. Progress of reaction was monitor by HPLC. After completion of reaction mass was filtered, distilled the acetone from filtrate & dissolved the residue obtained in toluene (2500 ml). Toluene layer was washed with brine & dried ($Na_2SO_4$). Toluene layer was filtered & cooled to −5 to −20° C. Conc hydrochloric acid (600 ml) was added slowly to above reaction mass at −5 to −20° C. & Stir for 1 hr at −5 to −20° C. Separated the two layers. Ethyl acetate (3000 ml) was added to aqueous layer. The pH of combined layers was adjusted to 5.0-6.5 by slowly adding potassium carbonate solution. Both the layers were separated (Store the ethyl acetate layer containing compound). Aqueous layer was extracted with ethyl acetate (3×2000 ml). The combined organic layer was washed with brine. Ethyl acetate was partially distilled (about 85% of original volume) from organic layer containing compound under reduced pressure. Reaction mass was cooled, filtered, washed with ethyl acetate (3×200 ml) & dried to get Olmesartan Medoxomil (150 g).

Example 3

Preparation of Olmesartan Medoxomil (In Situ)

4-(1-Hydroxy-1-methylethyl)-2-Propyl-1H-imidazole-5-carboxylic acid ethyl ester (100 g), N-(triphenylmethyl)-5-(4'-bromomethylbiphenyl-2-yl)tetrazole (250 g), potassium carbonate (170 g) & tetra butyl ammonium bromide (15 g) in acetone (2.5 L) were refluxed for 15 hours. The reaction mass was cooled & filtered to remove the salts. Salts were washed with acetone (300 ml). Acetone from combined filtrate was distilled completely & residue was refluxed with acetonitrile (500 ml). The reaction mass was cooled, filtered & solid after filtration was dissolved in isopropyl alcohol (1500 ml). Separately prepared solution of potassium hydroxide (180 g) in IPA (2.0 L) was added to above solution at room temperature. Reaction was stirred for 3 hrs at 30-40° C. Isopropyl alcohol was distilled under reduced pressure. Brine (1.0 L) & ethyl acetate (2.0 L) was added to the residue. After layer separation aqueous layer was extracted with ethyl acetate (3×1000 ml). Combined ethyl acetate layer was washed with sodium bicarbonate solution (2×2.0 L) & dried ($Na_2SO_4$). Ethyl acetate was distilled completely under reduced pressure. Acetone (4.0 L) was added to the residue & heated to reflux; the solution obtained was added to suspension of potassium carbonate (50 g), potassium iodide (15 g) & 4-chloromethyl-5-methyl-1,3-dioxol-2-one (75 g) in acetone (1500 ml) at reflux temperature. Reaction, mass was refluxed for 2-6 hrs. After competition of reaction, the reaction mass was filtered & the acetone was distilled from combined mother liquor. The residue obtained was dissolved in toluene (2.5 L) toluene layer was washed with brine (3×750 ml) & dried ($Na_2SO_4$). Toluene layer was filtered & cooled to 0 to −20° C. Conc. HCl (1.35 L) was added slowly to above reaction mass at −5 to −15° C. Stirred for 1 hr. The two layers were separated & ethyl acetate (3.0 L) was added to aqueous layer. The pH of combined layers was adjusted to 5.0-6.5 by adding potassium carbonate solution. Both the layers were separated (Store the ethyl acetate layer-containing compound) & aqueous layer was extracted with ethyl acetate (3×2.0 L). Combined organic layers were washed with brine. Ethyl acetate was distilled from organic layer containing compound under reduced pressure. The residue was dissolved in acetone (2.5 to 4 Lt) at reflux temperature. The solution was stirred with carbon & filtered, followed by partial distillation of acetone. The reaction mass was cooled slowly to 0-5° C. Filtered, washed with acetone (2×200 ml) & dried to get Olmesartan Medoxomil (115 g).

Purity: 99.1%.

Example 4

Preparation of Trityl Olmesartan Medoxomil (Insitu)

4-(1-Hydroxy-1-methylethyl)-2-Propyl-1H-imidazole-5-carboxylic acid ethyl ester (100 g), N-(triphenylmethyl)-5 (4'-bromomethylbiphenyl-2-yl)tetrazole (250 g), potassium carbonate (170 g) & tetra butyl ammonium bromide (15 g) in acetone (2.5 L) were refluxed for 15 hours. The reaction mass was cooled & filtered to remove the salts. Salts were washed with acetone (300 ml). Acetone from combine the filtrate & washings was distilled. The residue obtained was refluxed with acetonitrile (500 ml). The reaction mass was cooled, filtered & solid after filtration was dissolved in Isopropyl alcohol (1500 ml). Separately prepared solution of potassium hydroxide (180 g) in IPA (2.0 L) was added to above solution at room temperature. Reaction was stirred for 3 hrs at 30-40° C. Isopropyl alcohol was distilled under reduced pressure. Brine (1.0 L) & ethyl acetate (2.0 L) was added to the residue. After layer separation aqueous layer was extracted with ethyl acetate (3×1000 ml). Combined ethyl acetate layer was washed with sodium bicarbonate solution (2×2.0 L) & dried ($Na_2SO_4$). Ethyl acetate was distilled completely under reduced pressure. Acetone (4.0 L) was added to the residue & heated to reflux; the solution obtained was added to suspension of potassium carbonate (50 g), potassium iodide (15 g) & 4-chloromethyl-5-methyl-1,3-dioxol-2-one (75 g) in acetone (1500 ml) at reflux temperature. Reaction mass was refluxed for 2-6 hrs. After competition of reaction, the reaction mass was filtered & the acetone was distilled from combined mother liquor. The residue obtained was dissolved in toluene (2.5 L) toluene layer was washed with brine (3×750 ml) Toluene was removed under reduced pressure. Methanol (1.5 L) was added to the residue and stirred at 35° C. for 2 hr. Reaction mass was cooled to 0° C., filtered, washed with (2×500 ml) chilled methanol & dried to get pure Trityl Olmesartan Medoxomil (200 g)

Example 5

Preparation of ethyl-4-(1-hydroxy-1-methylethyl)-2-propyl-1-{4-[2-(trityl tetrazol-5-yl)phenyl]phenyl}methylimidazole-5-carboxylate 4-(1-Hydroxy-1-methylethyl)-2-propyl-1H-imidazole-5-carboxylic acid ethyl ester (100 g), N-(triphenylmethyl)-5-(4'-bromomethyl biphenyl-2-yl)tetrazole (250 g), potassium carbonate (170 g) & tetra butyl ammonium bromide (15 g) in acetone (2.5 L) were refluxed for 10-16 hours. Progress of reaction was monitor by HPLC. After completion of reaction, reaction mass was cooled and filtered to remove the salts. Inorganic salts were washed with acetone (300 mL). Acetone from combine the filtrate and washings was distilled. The residue obtained was crystallized in acetonitrile to get ethyl-4-(1-hydroxy-1-methylethyl)-2-propyl-1-{4-[2-(trityltetrazol-5-yl)phenyl]phenyl}methylimidazole-5-carboxylate (280 g).
HPLC Purity=98.5%

Example 6

Preparation of 4-(1-Hydroxy-1-methylethyl)-2-propyl-1-{4-[2-(trityltetrazol-5-yl)phenyl]phenyl}methylimidazole-5-carboxylic Acid Dihydrate Ethyl-4-(1-hydroxy-1-methylethyl)-2-propyl-1-{4-[2-(trityltetrazol-5-yl)phenyl]phenyl}methyl imidazole-5-carboxylate (100 g) was dissolved in isopropyl alcohol (500 ml). Separately prepared solution of potassium hydroxide (32 g) in IPA (1.0 L) was added slowly to above solution at room temperature. Reaction mass was stir for 2-4 hrs at 30-40° C. Isopropyl alcohol was distilled under reduced pressure. Water (400 mL), sodium chloride (40 g) & ethyl acetate (1.0 L) was added to the residue. Separate the two layers & aqueous layer was extracted with ethyl acetate (3×500 ml). Combined ethyl acetate layer was washed with sodium bicarbonate solution (3×500 mL) & dried ($Na_2SO_4$). Distilled off ethyl acetate under reduced pressure completely & residue thus obtained was recrystallized from acetonitrile to get 4-(1-hydroxy-1-methylethyl)-2-propyl-1-{4-[2-(trityltetrazol-5-yl)phenyl]phenyl}methylimidazole-5-carboxylic acid dihydrate (95 g).
HPLC purity=99.0%
Moisture Content ~5.0%.

Example 7

Preparation of Trityl Olmesartan Medoxomil 4-(1-Hydroxy-1-methylethyl)-2-propyl-1-{4-[2-(trityltetrazol-5-yl)phenyl]phenyl}methylimidazole-5-carboxylic acid dehydrate (100 g) was suspended in acetone (1 L) & heated to reflux; the solution obtained was added to suspension of potassium carbonate (15 g), potassium iodide (6 g) & 4-chloromethyl-5-methyl-1,3-dioxol-2-one (35 g) in acetone (500 mL) at reflux temperature. Reaction mass was refluxed for 2-6 hrs. After competition of reaction, the reaction mass was filtered & the acetone was distilled from combined mother liquor. The residue obtained was dissolved in toluene (1 L) toluene layer was washed with brine (3×250 mL). Toluene was removed under reduced pressure & residue thus obtained was recrystallized from methanol to give trityl Olmesartan Medoxomil (100 g).
HPLC purity=99.5%

Preparation of Olmesartan Medoxomil

Example 8

To a solution of (5-Methyl-2-oxo-1,3-dioxolen-4-yl)methyl-4-(1-hydroxy-1-methyl ethyl)-2-propyl-1-{4-[2-(trityltetrazol-5-yl)phenyl]phenyl}methylimidazole-5-carboxylate (5.0 g; 6.25 mmol) and toluene (20 ml) at 15-20° C. is added hydrochloric acid (30 ml). Reaction mass is stirred at 15-20° C. for about 15 minutes to 4 hours. The reaction is monitored by TLC. After completion of reaction layers are separated. Aqueous layer is washed with toluene (10 ml). Adjusted the pH of the aqueous layer to 5-6 using aqueous potassium carbonate solution (200 ml) and the compound is extracted using ethyl acetate (60 ml). Combined ethyl acetate layers are washed with brine. Finally crude product (3.1 g; 89.8%) is isolated by evaporation of solvent under reduced pressure.
Purity: 99.5%

Example 9

To a solution of (5-Methyl-2-oxo-1,3-dioxolen-4-yl)methyl-4-(1-hydroxy-1-methylethyl)-2-propyl-1-{4-[2-(trityltetrazol-5-yl)phenyl]phenyl}methylimidazole-5-carboxylate (10.0 g; 12.5 mmol) and ethyl Acetate (60 ml) at 15-20° C. is added hydrochloric acid (60 ml). Reaction mass is stirred at 15-20° C. for about 5 to 8 hours. The reaction is monitored by TLC. After completion of reaction, the reaction mass is cooled to 10° C. and water (20 ml) is added. Adjusted the pH of the aqueous layer to 5-6 using aqueous potassium carbonate solution (300 ml). Layers are separated. Combined organic layers are washed with brine. Finally crude product (6.2 g; 89.8%) is isolated by evaporation of solvent under reduced pressure.
Purity: 99.0%

Example 10

To solution of (5-Methyl-2-oxo-1,3-dioxolen-4-yl)methyl-4-(1-hydroxy-1-methyl ethyl)-2-propyl-1-{4-[2-(trityltetrazol-5-yl)phenyl]phenyl}methylimidazole-5-carboxylate (10.0 g; 12.5 mmol) and heptane (40 ml) at 15-20° C. is added hydrochloric acid (30 ml). Reaction mass is stirred at 0-10° C. for about 1 to 4 hours. The progress of reaction is monitored by TLC. After completion of reaction, layers are separated. Aqueous layer is washed with heptane (40 ml). Adjusted pH of the aqueous layer to 5-6 using 20% potassium carbonate solution (200 ml) and the compound is extracted using ethyl acetate (60 ml). Combined organic layer is washed with brine. Finally crude product (6.0 g; 76.8%) is isolated by evaporation of solvent under reduced pressure.

Purity: 99.2%

While the present invention has been described in terms of its specific embodiments, certain modifications and equivalents will be apparent to those skilled in the art and are intended to be included within the scope of the present invention.

We claim:

1. A process for the preparation of Olmesartan medoxomil which comprises
   i) alkylating ethyl 4-(1-hydroxy-1-methylethyl)-2-propylimidazole-5-carboxylate with 4-[2-(trityltetrazol-5-yl)phenyl]benzyl bromide in the presence of a catalyst and a base in an organic solvent to obtain ethyl 4-(1-hydroxy-1-methylethyl)-2-propyl-1-{4-[2-(trityl tetrazol-5-yl)phenyl]phenyl}methylimidazole-5-carboxylate,
   ii) hydrolyzing the ethyl 4-(1-hydroxy-1-methylethyl)-2-propyl-1-{4-[2-(trityl tetrazol-5-yl)phenyl]phenyl}methyl imidazole-5-carboxylate to obtain trityl Olmesartan dihydrate, iii) esterifying the trityl Olmesartan dihydrate with 4-chloromethyl-5-methyl-2-oxo-1,3-dioxolene in an organic solvent in the presence of a base and a catalyst to obtain trityl Olmesartan medoxomil, and
   iv) deprotecting the trityl Olmesartan medoxomil to obtain Olmesartan medoxomil.

2. The process according to claim 1, wherein the catalysts employed are selected from phase transfer catalysts.

3. The process according to claim 1, wherein the bases employed are selected from alkali metal carbonates, alkali metal hydrogen carbonates, alkali metal hydrides, alkali metal alkoxides, and organic amines.

4. The process according to claim 1, wherein the organic solvents used are selected from aromatic hydrocarbons, ethers, alcohols, amides, ketones, nitriles, sulfoxides, and halogenated aliphatic hydrocarbons.

5. A process for preparing Olmesartan medoxomil comprising:
   i) contacting trityl Olmesartan medoxomil with an acid in water and a water-immiscible organic solvent,
   ii) separating aqueous and organic layers,
   iii) adjusting the pH of the aqueous layer with a base,
   iv) extracting the resulting solution of step (iii) with water miscible organic solvents and
   v) isolating Olmesartan medoxomil.

6. The process according to claim 5, wherein the acid is selected from organic acids, oxoacids, and binary acids.

7. The process according to claim 5, wherein the water-immiscible organic solvents are selected from hydrocarbons, aliphatic solvents, ketones, and carboxylic esters.

8. The process according to claim 5 wherein the pH is adjusted with a base selected from sodium hydroxide, potassium hydroxide, calcium hydroxide, magnesium hydroxide, sodium carbonate, potassium carbonate, sodium bicarbonate, potassium bicarbonate, and calcium carbonate.

9. The process according to claim 5 wherein the extraction is performed using a water-immiscible organic solvent selected from ethyl ether, isopropyl ether, ethyl acetate, n-propyl acetate, methyl isobutyl ketone, cyclohexanone, tert-amyl alcohol, and 2-ethyl-1-hexanol.

10. Trityl Olmesartan dihydrate.

11. Trityl Olmesartan dihydrate as claimed in claim 10, wherein a moisture content is in the range of 4.0-6.0% w/w.

12. Use of Trityl Olmesartan dihydrate in the preparation of Olmesartan medoxomil, comprising the esterfication of trityl olmesartan dihydrate with 4-chloromethyl-5-methyl-2-oxo-1,3 dioxolane.

13. The process according to claim 8, wherein said base is selected from potassium carbonate and sodium bicarbonate.

14. The process according to claim 2, wherein the phase transfer catalysts are selected from tetrabutyl ammonium bromide, tetrabutyl ammonium iodide, tetrapropyl ammonium bromide, tri butyl benzyl ammonium bromide, tetraoctyl ammonium bromide, tetra butyl ammonium hydrogen sulphate, benzyl trimethyl ammonium chloride, benzyl triethyl ammonium chloride, tetrabutyl ammonium acetate and ethyl triphenyl phosphonium bromide, and the alkyl iodides are selected from potassium iodide, sodium iodide and lithium iodide.

15. The process according to claim 3, wherein the alkali metal carbonates are selected from sodium carbonate and potassium carbonate, the alkali metal hydrogen carbonates are selected from sodium hydrogen carbonate and potassium hydrogen carbonate, the alkali metal hydrides are selected from sodium hydride, potassium hydride and lithium hydride, the alkali metal alkoxides are selected from sodium methoxide, sodium ethoxide, potassium t-butoxide and lithium methoxide, and the organic amines are selected from triethylamine, pyridine and N-methyl morpholine.

16. The process according to claim 4, wherein the aromatic hydrocarbons are selected from benzene, toluene and xylene, the ethers are selected from tetrahydrofuran and dioxane, the alcohols are selected from methanol, ethanol and t-butanols, the amides are selected from N,N-dimethylacetamide, N,N-dimethylformamide and N-methyl-2-pyrrrolidinone, the ketones are selected from acetone and methyl ethyl ketone, the nitrile is acetonitrile, the sulfoxide is dimethyl sulfoxide, and the halogenated aliphatic hydrocarbons are methylene chloride.

17. The process according to claim 6, wherein the organic acids are selected from formic acid, acetic acid, benzoic acid and oxalic acid, the oxoacids are selected from sulfuric acid, sulfurous acid, p-toluene sulfonic acid, nitric acid, nitrous acid, phosphoric acid and carbonic acid, and the binary acids are selected from hydrofluoric acid, hydrochloric acid, hydrobromic acid, hydrocyanic acid and hydrosulfuric acid.

18. The process according to claim 7, wherein the hydrocarbons are selected from benzene, cyclohexane, toluene and xylene, the aliphatic solvents are selected from halocarbons, the ketone is methyl isobutyl ketone, and the carboxylic ester is ethyl acetate.

19. The process according to claim 18, wherein the hydrocarbons are selected from methylene chloride and chloroform.

* * * * *